(12) United States Patent
Terane

(10) Patent No.: US 11,986,583 B2
(45) Date of Patent: May 21, 2024

(54) OXYGENATOR

(71) Applicant: TERUMO KABUSHIKI KAISHA, Tokyo (JP)

(72) Inventor: Shotaro Terane, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 577 days.

(21) Appl. No.: 17/322,981

(22) Filed: May 18, 2021

(65) Prior Publication Data

US 2021/0268163 A1 Sep. 2, 2021

Related U.S. Application Data

(63) Continuation of application No. PCT/JP2019/045478, filed on Nov. 20, 2019.

(30) Foreign Application Priority Data

Nov. 27, 2018 (JP) ................................ 2018-221230

(51) Int. Cl.
*A61M 1/16* (2006.01)
*A61M 1/36* (2006.01)
*B01D 69/08* (2006.01)

(52) U.S. Cl.
CPC ........ *A61M 1/1698* (2013.01); *A61M 1/1641* (2014.02); *A61M 1/3623* (2022.05);
(Continued)

(58) Field of Classification Search
CPC .............. A61M 1/1698; A61M 1/1641; A61M 1/3623; A61M 2202/0208;
(Continued)

(56) References Cited

U.S. PATENT DOCUMENTS 5,055,198 A * 10/1991 Shettigar ............... A61M 1/631
604/35
5,863,501 A * 1/1999 Cosentino ........... A61M 1/1698
422/46

(Continued)

FOREIGN PATENT DOCUMENTS

| JP | 2003111837 A | 4/2003 |
|----|--------------|--------|
| JP | 2007190218 A | 8/2007 |
| WO | 2008120747 A1 | 9/2008 |

OTHER PUBLICATIONS

Written Opinion of ISA, PCT/JP2019/045478, dated Jan. 7, 2020.
International Search Report, PCT/JP2019/045478, dated Jan. 7, 2020.

*Primary Examiner* — Jessica Arble
*Assistant Examiner* — Alessandro R Del Priore
(74) *Attorney, Agent, or Firm* — MacMillan, Sobanski & Todd, LLC

(57) ABSTRACT

An oxygenator includes: a housing; a bubble-removing hollow fiber membrane layer removing a bubble; a gas-exchanging hollow fiber membrane layer exchanging a gas with blood; and a discharge port to discharge the bubble removed by the bubble-removing hollow fiber membrane layer to the outside of the housing. The oxygenator further includes a gas permeable portion that is arranged between the discharge port and an end portion of the bubble-removing hollow fiber membrane layer, is formed by a member having gas permeability, and allows passage of the bubble removed by the bubble-removing hollow fiber membrane layer without allowing passage of plasma leaking through the bubble-removing hollow fiber membrane layer. A plasma capture chamber that captures the plasma leaking through the bubble-removing hollow fiber membrane layer is formed between the end portion of the bubble-removing hollow fiber membrane layer and the gas permeable portion.

9 Claims, 2 Drawing Sheets

(52) U.S. Cl.
CPC ..... *B01D 69/08* (2013.01); *A61M 2202/0208* (2013.01); *A61M 2205/073* (2013.01); *B01D 2325/20* (2013.01)

(58) Field of Classification Search
CPC .......... A61M 2205/073; A61M 1/3643; A61M 1/3627; A61M 2202/0415; A61M 2205/7536; B01D 69/08; B01D 2325/20; B01D 2315/22; B01D 63/02; B01D 2313/08
See application file for complete search history.

(56) References Cited

U.S. PATENT DOCUMENTS

| | | | | |
|---|---|---|---|---|
| 6,495,101 | B1 * | 12/2002 | Yokoyama | B01D 67/0088 604/6.14 |
| 7,749,435 | B2 * | 7/2010 | Ogihara | A61M 1/1698 604/6.11 |
| 7,927,544 | B2 * | 4/2011 | Federspiel | A61M 60/113 604/6.14 |
| 8,147,753 | B2 | 4/2012 | Tanaka et al. | |
| 8,647,569 | B1 * | 2/2014 | Federspiel | A61M 60/825 604/6.14 |
| 2005/0077228 | A1 * | 4/2005 | Pasqualini | A61M 1/1698 210/321.72 |
| 2007/0166189 | A1 * | 7/2007 | Ogihara | A61M 1/3623 422/45 |
| 2010/0114004 | A1 * | 5/2010 | Tanaka | A61M 1/1625 604/6.13 |
| 2014/0030149 | A1 * | 1/2014 | Takeuchi | A61M 1/3623 422/48 |

\* cited by examiner

OXYGENATOR

CROSS REFERENCE TO RELATED APPLICATIONS

This application is a continuation of PCT Application No. PCT/JP2019/045478, filed Nov. 20, 2019, based on and claiming priority to Japanese Application No. 2018-221230, filed Nov. 27, 2018, both of which are incorporated herein by reference in their entirety.

BACKGROUND OF THE INVENTION

The present invention relates to an oxygenator.

In a case where extracorporeal membrane oxygenation (ECMO) is used, it is necessary to perform priming of an extracorporeal circulation circuit including an oxygenator as easily and as quickly as possible particularly when extracorporeal cardiopulmonary resuscitation (ECPR) is required.

Conventionally, there is proposed an oxygenator in which a bubble-removing hollow fiber membrane layer that removes bubbles is housed in a housing (see published application JP2003-111837A). According to this oxygenator, the removal of bubbles in an extracorporeal circulation circuit including the oxygenator can be promoted, and the priming can be speeded up.

The oxygenator described in JP2003-111837A does not take any measure against plasma leaking through the bubble-removing hollow fiber membrane layer. The leakage of a relatively small amount of plasma to the outside of the oxygenator is not a problem. However, the continuation of the plasma leakage to the outside (plasma leak) for a long period of time is a problem that is not ignorable for the oxygenator that circulates blood for a relatively long period of time.

SUMMARY OF THE INVENTION

Therefore, an object of the present invention is to provide an oxygenator capable of speeding up priming and limiting a leakage of plasma.

An oxygenator according to one aspect of the present invention includes: a housing; a bubble-removing hollow fiber membrane layer which is housed in the housing and removes a bubble; a gas-exchanging hollow fiber membrane layer which is housed in the housing and exchanges a gas with a blood; and a discharge port which is formed in the housing to discharge the bubble removed by the bubble-removing hollow fiber membrane layer to the outside of the housing. The oxygenator further includes: a gas permeable portion that is arranged between the discharge port and an end portion of the bubble-removing hollow fiber membrane layer, is formed by a member having gas permeability, and allows passage of the bubble removed by the bubble-removing hollow fiber membrane layer without allowing passage of plasma leaking through the bubble-removing hollow fiber membrane layer; and a plasma capture chamber which forms an isolated partitioned between the end portion of the bubble-removing hollow fiber membrane layer and the gas permeable portion and captures the plasma leaking through the bubble-removing hollow fiber membrane layer.

According to the oxygenator of the present invention, the bubble removed by the bubble-removing hollow fiber membrane layer passes through the gas permeable portion formed by the member having gas permeability and is discharged from the discharge port to the outside of the housing. On the other hand, the plasma leaking through the bubble-removing hollow fiber membrane layer is captured in the plasma capture chamber without passing through the gas permeable portion and does not leak to the outside of the housing. Therefore, it is possible to provide the oxygenator capable of promoting the bubble removal to speed up the priming and limiting the plasma leakage.

DETAILED DESCRIPTION

Hereinafter, an embodiment of the present invention will be described with reference to each drawing. Dimensional ratios of the drawings are exaggerated for the convenience of description and may differ from actual ratios in some cases.

Figure 1:
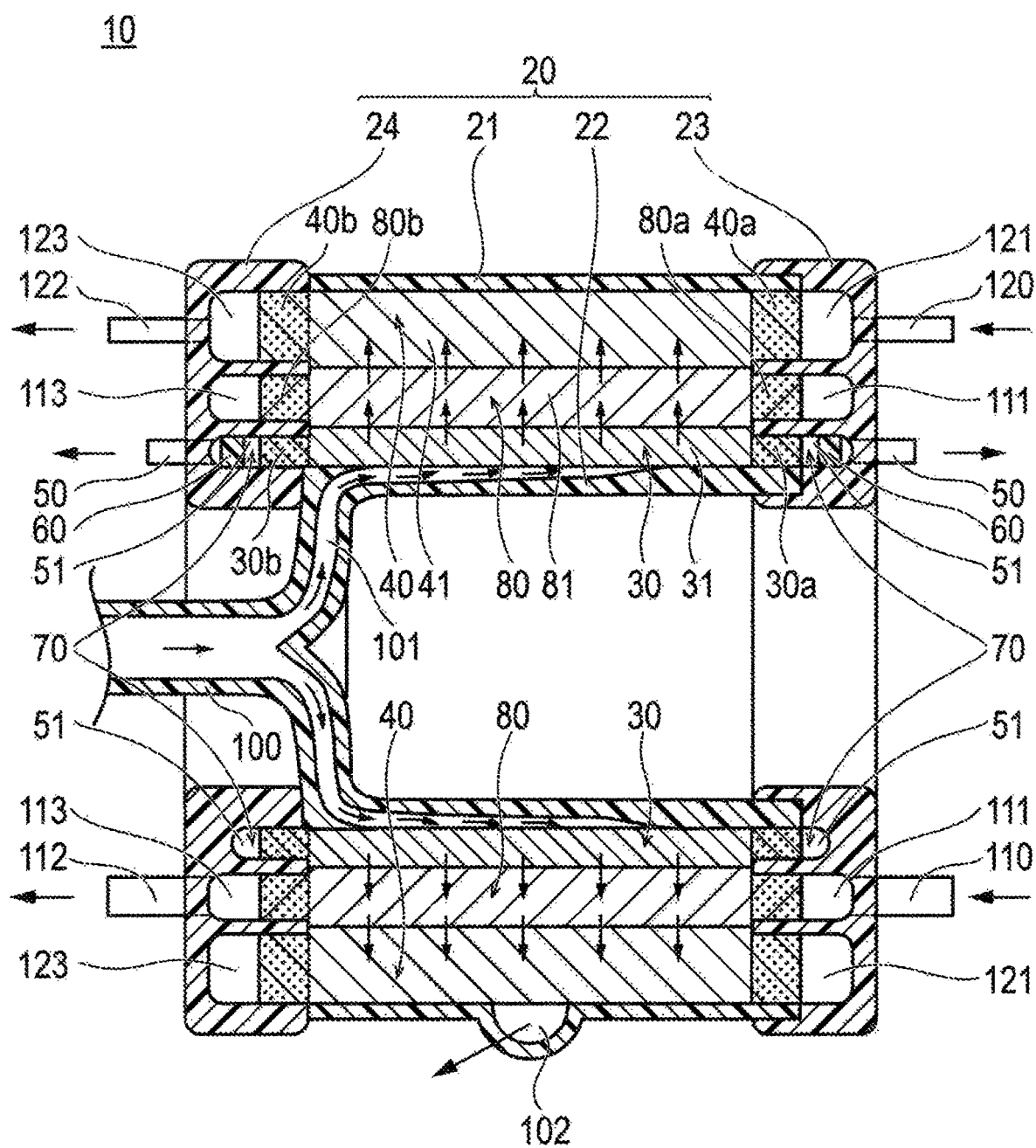
FIG. 1 is a cross-sectional view illustrating an oxygenator according to an embodiment.
Figure 2:
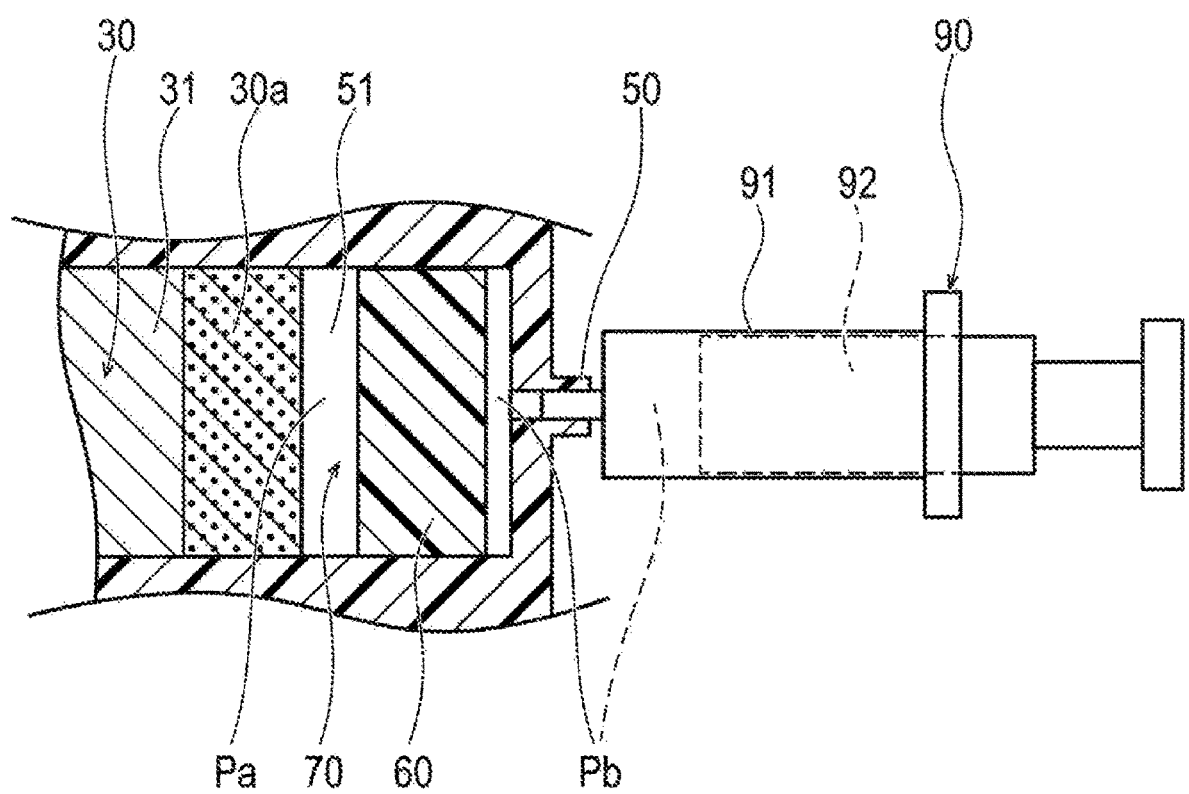
FIG. 2 is a cross-sectional view of a main part illustrating a state where a syringe as a negative pressure applying unit is connected to a discharge port of the oxygenator.

As illustrated in FIGS. 1 and 2, an oxygenator 10 according to the embodiment briefly includes: a housing 20; a bubble-removing hollow fiber membrane layer 31 which is housed in the housing 20 and removes a bubble; a gas-exchanging hollow fiber membrane layer 41 which is housed in the housing 20 and exchanges a gas with a blood; and a discharge port 50 which is formed in the housing 20 to discharge the bubble removed by the bubble-removing hollow fiber membrane layer 31 to the outside of the housing 20. The oxygenator 10 further includes a gas permeable portion 60 that is arranged between the discharge port 50 and an end portion of the bubble-removing hollow fiber membrane layer 31, is formed by a member having gas permeability, and allows passage of the bubble removed by the bubble-removing hollow fiber membrane layer 31 without allowing passage of plasma leaking through the bubble-removing hollow fiber membrane layer 31. A plasma capture chamber 70 that captures the plasma leaking through the bubble-removing hollow fiber membrane layer 31 is formed between the end portion of the bubble-removing hollow fiber membrane layer 31 and the gas permeable member 60. Hereinafter, the oxygenator 10 according to the embodiment will be described in detail.

The housing 20 has an outer cylinder member 21 having a cylindrical shape, an inner cylinder member 22, a first header 23, and a second header 24.

The outer cylinder member 21 is provided so as to surround the inner cylinder member 22. The inner cylinder member 22 is formed with a flow path 101 that communicates with a blood inflow port 100. The outer cylinder member 21 is formed with a blood outflow port 102. The first header 23 is attached to one end portions of the outer cylinder member 21 and the inner cylinder member 22, and the second header 24 is attached to the other end portions thereof.

The first header 23 is formed with the bubble discharge port 50 and a bubble discharge path 51. The discharge port 50 and the discharge path 51 communicate with each other. The first header 23 is formed with a heat transfer medium inflow port 110 and a heat transfer medium inflow path 111. The inflow port 110 and the inflow path 111 communicate with each other. The first header 23 is formed with a gas inflow port 120 and a gas inflow path 121. The inflow port 120 and the inflow path 121 communicate with each other.

The bubble discharge path 51, the heat transfer medium inflow path 111, and the gas inflow path 121 are formed in the first header 23 so as to have a ring shape, and are separated so as not to communicate with each other.

Similarly, the second header 24 is also formed with the bubble discharge port 50 and the bubble discharge path 51. The discharge port 50 and the discharge path 51 communicate with each other. The second header 24 is formed with a heat transfer medium outflow port 112 and a heat transfer medium outflow path 113. The outflow port 112 and the outflow path 113 communicate with each other. The second header 24 is formed with a gas outflow port 122 and a gas outflow path 123. The outflow port 122 and the outflow path 123 communicate with each other.

The bubble discharge path 51, the heat transfer medium outflow path 113, and the gas outflow path 123 are formed in the second header 24 so as to have a ring shape, and are separated so as not to communicate with each other.

The housing 20 is preferably transparent enough to visually recognize the blood flow inside. A material forming the housing 20 is not particularly limited, but it is possible to use, for example, polyolefins such as polyethylene and polypropylene, ester resins such as polyethylene terephthalate, styrene resins such as polystyrene, MS resins, and MBS resins, polycarbonate, and the like.

Inside the housing 20, a bubble removing unit 30, a heat exchange unit 80, and a gas exchange unit 40 are arranged in order from the upstream side in a blood flow direction.

The bubble removing unit 30 is arranged in a tubular shape around the inner cylinder member 22. One end portion 30a of the bubble removing unit 30 is liquid-tightly fixed to the bubble discharge path 51 in the first header 23by, for example, a potting agent. The other end portion 30b of the bubble removing unit 30 is liquid-tightly fixed to the bubble discharge path 51 in the second header 24by, for example, a potting agent.

The heat exchange unit 80 is arranged in a tubular shape around the bubble removing unit 30. One end portion 80a of the heat exchange unit 80 is liquid-tightly fixed to the heat transfer medium inflow path 111 by, for example, a potting agent. The other end portion 80b of the heat exchange unit 80 is liquid-tightly fixed to the heat transfer medium outflow path 113by, for example, a potting agent.

The gas exchange unit 40 is arranged in a tubular shape around the heat exchange unit 80. One end portion 40a of the gas exchange unit 40 is liquid-tightly fixed to the gas inflow path 121by, for example, a potting agent. The other end portion 40b of the gas exchange unit 40 is liquid-tightly fixed to the gas outflow path 123by, for example, a potting agent.

Blood introduced through the blood inflow port 100 fills the inside of the housing 20, bubbles are removed in the bubble removing unit 30, the temperature is adjusted in the heat exchange unit 80, and gas exchange is performed in the gas exchange unit 40. At the time of priming, bubbles in an extracorporeal circulation circuit including the oxygenator 10 are removed by the bubble removing unit 30.

When introduced from the blood inflow port 100, the blood passes through the flow path 101 and is guided to the bubble removing unit 30. The blood moves radially outward through the heat exchange unit 80 and the gas exchange unit 40.

The bubble removing unit 30 has a bubble-removing hollow fiber membrane layer 31 formed of a plurality of bundles of hollow fiber for bubble removal. Blood passes through the bubble removing unit 30 through a gap between the hollow fibers. Each of the hollow fibers is wound around the inner cylinder member 22 so as to connect the bubble discharge paths 51 on both sides. Each of the hollow fibers communicates with the bubble discharge path 51 at both end portions. The blood comes into contact with the hollow fibers while moving through the gap between the hollow fibers. A fine hole communicating with the inside is formed on a peripheral wall of the hollow fiber, and bubbles in the blood are taken into the inside of the hollow fiber through the hole when the blood comes into contact with the hollow fiber. After flowing inside the hollow fiber, bubbles exit the bubble discharge path 51, further pass through the gas permeable portion 60, and are discharged to the outside from the discharge port 50. Some of plasma components in the blood are taken into the inside of the hollow fiber through the hole in the peripheral wall of the hollow fiber.

In the end portions 30a and 30b of the bubble removing unit 30, the gap between the hollow fibers is filled with, for example, a potting agent to be in a liquid-tight state. Therefore, the blood does not flow out to the bubble discharge path 51.

The heat exchange unit 80 has a heat-exchanging hollow fiber membrane layer 81 formed of a plurality of bundles of hollow fibers for heat exchange. Blood passes through the heat exchange unit 80 through a gap between the hollow fibers. Each of the hollow fibers is wound in the circumferential direction with respect to a long-axis direction of the inner cylinder member 22 from a side of the heat transfer medium inflow path 111 to a side of the heat transfer medium outflow path 113. Each of the hollow fibers communicates with the heat transfer medium inflow path 111 at one end portion and communicates with the heat transfer medium outflow path 113 at the other end portion. A heat transfer medium is introduced from the heat transfer medium inflow port 110, passes through the inflow path 111, and enters the inside of the hollow fiber. After flowing inside the hollow fiber, the heat transfer medium exits the outflow path 113 and flows out from the heat transfer medium outflow port 112. The blood moves in the gap between the hollow fibers, comes into contact with the hollow fibers, and exchanges heat with the heat transfer medium flowing inside the hollow fibers. The heat transfer medium is, for example, hot or cold water adjusted to a predetermined temperature, but is not limited thereto.

In the end portions 80a and 80b of the heat exchange unit 80, the gap between the hollow fibers is filled with, for example, a potting agent to be in a liquid-tight state. Therefore, the blood does not flow out to the inflow path 111 and the outflow path 113 of the heat transfer medium, and the heat transfer medium does not enter the gap between the hollow fibers and does not mix with the blood.

The gas exchange unit 40 has the gas-exchanging hollow fiber membrane layer 41 formed of a bundle of a plurality of hollow fibers for gas exchange. Blood passes through the gas exchange unit 40 through a gap between the hollow fibers. Each of the hollow fibers extends substantially linearly from a side of the gas inflow path 121 to a side of the gas outflow path 123. Each of the hollow fibers communicates with the gas inflow path 121 at one end portion and communicates with the gas outflow path 123 at the other end portion. A gas is introduced from the gas inflow port 120, passes through the inflow path 121, and enters the inside of the hollow fiber. After flowing inside the hollow fiber, the gas exits the outflow path 123 and flows out from the gas outflow port 122 to the outside. The blood comes into contact with the hollow fibers while moving through the gap between the hollow fibers. A fine hole communicating with the inside is formed in a peripheral wall of the hollow fiber, and oxygen, which is the gas flowing inside the hollow fiber, is taken into the blood through the hole when the blood comes into contact with the hollow fiber. Further, at this time, carbon dioxide in the blood is taken into the inside of the hollow fiber.

In the end portions 40a and 40b of the gas exchange unit 40, the gap between the hollow fibers is filled with, for example, a potting agent to be in a liquid-tight state. Therefore, the blood does not flow out to the inflow path 121 and the outflow path 123 of the gas, and the gas does not enter the gap between the hollow fibers and does not mix with the blood. The blood is appropriately temperature-adjusted and gas-exchanged by the heat exchange unit 80 and the gas exchange unit 40, respectively, and then flows out through the blood outflow port 102.

The gas permeable member portion 60 is arranged at a position that blocks direct communication between the discharge port 50 and the end portion of the bubble-removing hollow fiber membrane layer 31. The gas permeable portion 60 is formed using a member having gas permeability. The gas permeable portion 60 exhibits a function of allowing passage of bubbles removed by the bubble-removing hollow fiber membrane layer 31 while preventing passage of plasma leaking through the bubble-removing hollow fiber membrane layer 31. The member having gas permeability that forms the gas permeable portion 60 is not limited as long as the above function can be exhibited, but it is possible to use, for example, silicone rubber, more preferably polydimethylsiloxane (PDMS).

The plasma capture chamber 70 is a partition disposed between the end portion of the bubble-removing hollow fiber membrane layer 31 and the gas permeable portion 60 in the bubble discharge path 51 in the first header 23 and the bubble discharge path 51 in the second header 24. Some of plasma components of blood leak through the bubble-removing hollow fiber membrane layer 31, but such discharged plasma is captured in the plasma capture chamber 70. The internal volume of the plasma capture chamber 70 is preferably kept to the degree that allows the volume of leaked plasma to be negligible with respect to the body fluid volume of a patient.

As illustrated in FIG. 2, the oxygenator 10 further includes a negative pressure applying unit 90 connected to the discharge port 50, the negative pressure applying unit 90 applying a negative pressure to the bubble-removing hollow fiber membrane layer 31. The amount of gas per unit time that passes through the gas permeable portion 60 depends on a pressure difference (Pa−Pb) between a pressure Pa on the inflow side (the side of the bubble-removing hollow fiber membrane layer 31) and a pressure Pb on the outflow side (the side opposite to the bubble-removing hollow fiber membrane layer 31) of the gas permeable portion 60. As the pressure Pb on the outflow side is lower than the pressure Pa on the inflow side, the amount of gas passing through the gas permeable portion 60 per unit time can be increased. Bubbles can easily pass through the gas permeable portion 60 by applying the negative pressure to the bubble-removing hollow fiber membrane layer 31, and the discharge of the bubbles can be speeded up.

The negative pressure applying unit 90 can be configured using a syringe 91. The negative pressure is applied to the bubble-removing hollow fiber membrane layer 31 via the gas permeable portion 60 by a suction operation of the syringe 91 to pull a piston 92 of the syringe 91. Although it is possible to apply an electrical negative pressure applying device as the negative pressure applying unit 90, the negative pressure can be applied to the bubble-removing hollow fiber membrane layer 31 with a simple structure and a simple operation if the syringe 91 is applied as the negative pressure applying unit 90.

It is preferable that the gas permeable portion 60 and the syringe 91 be configured to be capable of sustaining the negative pressure applied by one suction operation of the syringe 91 for 5 minutes or more and less than 30 minutes. The priming of the extracorporeal circulation circuit including the oxygenator 10 is generally performed for 5 minutes or more and less than 30 minutes. Therefore, bubbles in the extracorporeal circulation circuit including the oxygenator 10 can be sufficiently removed in the priming with the configuration capable of sustaining the applied negative pressure for 5 minutes or more and less than 30 minutes. In order to sustain the negative pressure for a predetermined time, the volume (area and thickness dimension) of the gas permeable portion 60, the gas permeability performance of the gas permeable portion 60, the internal volume of the plasma capture chamber 70, the internal volume between the gas permeable portion 60 and the syringe 91, the magnitude of the negative pressure to be applied at the start of priming, and the like are selected.

Note that the suction operation of the syringe 91 can be repeated during priming. The suction operation of the syringe 91 can be repeated even during blood circulation.

After the application of the negative pressure is ended, it is unnecessary to attach a cap or the like to the discharge port 50 from which the syringe 91 has been removed. The discharge port 50 may remain open to the atmosphere.

Next, an operational effect of the oxygenator 10 of the present embodiment will be described.

When priming the extracorporeal circulation circuit including the oxygenator 10, the syringe 91 is connected to the discharge port 50 of the oxygenator 10, and the piston 92 of the syringe 91 is pulled. The negative pressure applied to the bubble-removing hollow fiber membrane layer 31 by one suction operation of the syringe 91 is sustained for 5 minutes or more and less than 30 minutes.

When a priming solution such as physiological saline is circulated, the priming solution passes through the gap between the hollow fibers in the bubble-removing hollow fiber membrane layer 31 of the bubble removing unit 30. The priming solution comes into contact with the hollow fibers while moving through the gap between the hollow fibers. Bubbles contained in the priming solution are taken into the inside of the hollow fibers through the fine holes in the peripheral walls of the hollow fibers. After flowing inside the hollow fibers, the bubbles exit the bubble discharge path 51, further pass through the gas permeable portion 60, and are discharged from the discharge port 50 to the outside (inside the syringe 91).

Since the bubble-removing hollow fiber membrane layer 31 is subjected to the negative pressure, the bubbles easily pass through the gas permeable portion 60, so that the removal of bubbles is promoted. As a result, the priming can be speeded up.

Since the syringe 91 is applied as the negative pressure applying unit 90, the negative pressure can be applied to the bubble-removing hollow fiber membrane layer 31 with a simple structure and a simple operation as compared with the case where the electrical negative pressure applying device is applied.

Furthermore, the applied negative pressure can be sustained for 5 minutes or more and less than 30 minutes, and thus, the bubbles in the extracorporeal circulation circuit including the oxygenator 10 can be sufficiently removed in the priming.

When the priming is complete, blood circulates in the extracorporeal circulation circuit including the oxygenator 10. The blood is introduced from the blood inflow port 100, passes through the flow path 101, and is guided to the bubble removing unit 30. The blood further moves radially outward through the heat exchange unit 80 and the gas exchange unit 40.

The blood comes into contact with the hollow fibers while moving through the gap between the hollow fibers in the bubble-removing hollow fiber membrane layer 31 in the bubble removing unit 30. Bubbles contained in the blood are taken into the inside of the hollow fibers through the fine holes in the peripheral walls of the hollow fibers. After flowing inside the hollow fibers, the bubbles exit the bubble discharge path 51, further pass through the gas permeable portion 60, and are discharged from the discharge port 50 to the outside (inside the syringe 91).

Some of plasma components in the blood are taken into the inside of the hollow fiber through the hole in the peripheral wall of the hollow fiber. The plasma leaking through the bubble-removing hollow fiber membrane layer 31 flows inside the hollow fibers, then exits the bubble discharge path 51, and further reaches the gas permeable portion 60. Since the gas permeable portion 60 does not allow the passage of plasma, the plasma is captured in the plasma capture chamber 70 without passing through the gas permeable portion 60. The plasma does not leak to the outside of housing 20.

The blood that has passed through the bubble removing unit 30 comes into contact with the hollow fibers while moving through the gap between the hollow fibers in the heat-exchanging hollow fiber membrane layer 81 of the heat exchange unit 80. The blood exchanges heat with a heat transfer medium flowing inside the hollow fiber to be temperature-adjusted.

The blood that has passed through the heat exchange unit 80 comes into contact with the hollow fibers while moving through the gap between the hollow fibers in the gas-exchanging hollow fiber membrane layer 41 of the gas exchange unit 40. Oxygen flowing inside the hollow fiber is taken into the blood, and carbon dioxide in the blood is taken into the inside of the hollow fiber. After the gas exchange, the blood flows out into the extracorporeal circulation circuit through the blood outflow port 102.

As described above, the oxygenator 10 of the present embodiment includes: the housing 20; the bubble-removing hollow fiber membrane layer 31; the gas-exchanging hollow fiber membrane layer 41; and the discharge port 50 to discharge the bubble removed by the bubble-removing hollow fiber membrane layer 31 to the outside of the housing 20. The oxygenator 10 further includes the gas permeable portion 60 that is arranged between the discharge port 50 and the end portion of the bubble-removing hollow fiber membrane layer 31, is formed by the member having gas permeability, and allows the passage of the bubble removed by the bubble-removing hollow fiber membrane layer 31 without allowing the passage of plasma leaked through the bubble-removing hollow fiber membrane layer 31. The plasma capture chamber 70 that captures the plasma leaked through the bubble-removing hollow fiber membrane layer 31 is formed between the end portion of the bubble-removing hollow fiber membrane layer 31 and the gas permeable portion 60.

According to the oxygenator 10 configured in this manner, the bubble removed by the bubble-removing hollow fiber membrane layer 31 passes through the gas permeable portion 60 formed by the member having gas permeability and is discharged from the discharge port 50 to the outside of the housing 20. On the other hand, the plasma leaking through the bubble-removing hollow fiber membrane layer 31 is captured in the plasma capture chamber 70 without passing through the gas permeable portion 60 and does not leak to the outside of the housing 20. Therefore, it is possible to provide the oxygenator 10 capable of promoting the bubble removal to speed up the priming and limiting the plasma leakage.

Since the gas permeable portion 60 is arranged between the discharge port 50 and the end portion of the bubble-removing hollow fiber membrane layer 31, the negative pressure for removing bubbles can be continuously applied when the pressure on the discharge port 50 side is reduced. Therefore, bubbles generated after a certain period of time can be quickly discharged.

Since the plasma capture chamber 70 is an isolated partition, no further amount of plasma leaks to the outside by filling the plasma capture chamber 70 with plasma even in the oxygenator 10 that circulates blood for a relatively long period of time. Therefore, it is possible to prevent the leakage of plasma to the outside (plasma leakage) from occurring over a long period of time.

It is preferable that the oxygenator 10 further have the negative pressure applying unit 90 which is connected to the discharge port 50 and applies the negative pressure to the bubble-removing hollow fiber membrane layer 31.

With this configuration, bubbles can easily pass through the gas permeable portion 60, and the discharge of the bubbles can be speeded up.

The negative pressure applying unit 90 is preferably configured using the syringe 91.

With this configuration, the negative pressure can be applied to the bubble-removing hollow fiber membrane layer 31 with a simple structure and a simple operation.

It is preferable that the gas permeable portion 60 and the syringe 91 be configured to be capable of sustaining the negative pressure applied by one suction operation of the syringe 91 for 5 minutes or more and less than 30 minutes.

With this configuration, bubbles in the extracorporeal circulation circuit including the oxygenator 10 can be sufficiently removed in the priming.

Although the oxygenator 10 according to the present invention has been described through the embodiment, the present invention is not limited to only the configurations that have been described in the embodiment but can be appropriately changed based on the description of the claims.

For example, the embodiment in which the discharge port 50, the gas permeable portion 60, and the plasma capture chamber 70 are formed in each of the first header 23 and the second header 24 has been illustrated, but the discharge port 50, the gas permeable portion 60, and the plasma capture chamber 70 could be formed in only one of the headers.

Further, the oxygenator 10 having the heat exchange unit 80 inside the housing 20 has been described, but the present invention can be applied to the oxygenator 10 that is provided with a heat exchange unit externally.

What is claimed is:

1. An oxygenator for treating a flow of blood, comprising:
a housing;
a bubble-removing hollow fiber membrane layer disposed in the housing and configured to remove bubbles from the blood;
a gas-exchanging hollow fiber membrane layer disposed in the housing and configured to exchange a gas with the blood;

a discharge port which is formed in the housing to discharge the bubbles removed by the bubble-removing hollow fiber membrane layer to an outside of the housing;

a gas permeable member which is arranged between the discharge port and an end portion of the bubble-removing hollow fiber membrane layer, wherein the gas permeable member allows passage of the bubbles removed by the bubble-removing hollow fiber membrane layer without allowing passage of a plasma leaking through the bubble-removing hollow fiber membrane layer; and a plasma capture chamber which is a partition between the end portion of the bubble-removing hollow fiber membrane layer and the gas permeable member and captures the plasma leaking through the bubble-removing hollow fiber membrane layer.

2. The oxygenator according to claim 1, further comprising a negative pressure applying unit which is connected to the discharge port and applies a negative pressure to the bubble-removing hollow fiber membrane layer via the gas permeable member.

3. The oxygenator according to claim 2, wherein the negative pressure applying unit is comprised of a syringe.

4. The oxygenator according to claim 3, wherein the gas permeable member and the syringe are configured to sustain a negative pressure applied by one suction operation of the syringe for 5 minutes or more and less than 30 minutes.

5. A method of treating blood in an oxygenator, comprising the steps of:
providing a flow of blood to an inlet of an oxygenator housing;
directing the flow of blood to a bubble-removing hollow fiber membrane layer disposed in the housing and configured to remove bubbles from the blood;
directing the flow of blood to a gas-exchanging hollow fiber membrane layer disposed in the housing and configured to exchange a gas with the blood;
directing the bubbles removed by the bubble-removing hollow fiber membrane layer through a gas permeable member which is disposed at an end portion of the bubble-removing hollow fiber membrane layer, wherein the gas permeable member allows passage of the bubbles removed by the bubble-removing hollow fiber membrane layer without allowing passage of a plasma leaking through the bubble-removing hollow fiber membrane layer;
removing the bubbles passing through the gas permeable member via a discharge port which is formed in the housing; and
capturing the plasma leaking through the bubble-removing hollow fiber membrane layer in a plasma capture chamber which is a partition between the end portion of the bubble-removing hollow fiber membrane layer and the gas permeable member.

6. The method of claim 5 further comprising the step of:
applying a suction to the discharge port to generate a negative pressure to the bubble-removing hollow fiber membrane layer via the gas permeable member.

7. The method of claim 6 wherein the step of applying a suction is comprised of connecting a negative pressure applying unit to the discharge port.

8. The method of claim 7 wherein the negative pressure applying unit is comprised of a syringe, and wherein the step of applying a suction is comprised of pulling a piston of the syringe.

9. The method of claim 8 wherein:
wherein the gas permeable member and the syringe are configured to sustain a negative pressure applied by one suction operation of the piston for 5 minutes or more and less than 30 minutes.

* * * * *